United States Patent [19]

Terhune

[11] Patent Number: 4,520,654
[45] Date of Patent: Jun. 4, 1985

[54] METHOD AND APPARATUS FOR DETECTING HYDROGEN, OXYGEN AND WATER VAPOR CONCENTRATIONS IN A HOST GAS

[75] Inventor: James H. Terhune, San Jose, Calif.

[73] Assignee: General Electric Company, San Jose, Calif.

[21] Appl. No.: 475,340

[22] Filed: Mar. 14, 1983

[51] Int. Cl.³ .................................... G01N 29/02
[52] U.S. Cl. ............................... 73/24; 73/1 G; 364/497; 376/256
[58] Field of Search ............. 73/24, 32 A, 1 G; 376/252, 256; 364/497, 498, 499

[56] References Cited

U.S. PATENT DOCUMENTS

| | | | |
|---|---|---|---|
| 2,984,097 | 5/1961 | Kniazuk et al. | 73/24 |
| 3,429,177 | 2/1969 | Webb | 73/24 |
| 3,468,157 | 9/1969 | Burk et al. | 73/24 |
| 3,724,484 | 4/1973 | Turman | 73/24 |
| 3,789,655 | 2/1974 | Passeri | 73/24 |
| 3,805,590 | 4/1974 | Ringwall et al. | 73/24 |
| 3,902,365 | 9/1975 | Knauth | 73/32 A |
| 3,977,394 | 8/1976 | Jones et al. | 73/23 |
| 3,981,176 | 9/1976 | Jacobs | 73/24 |
| 4,119,950 | 10/1978 | Redding | 73/24 |
| 4,155,246 | 5/1979 | Dempster et al. | 73/24 |
| 4,220,040 | 9/1980 | Noguchi et al. | 73/24 |
| 4,235,099 | 11/1980 | Ishizaka | 73/32 A |
| 4,236,827 | 12/1980 | Horiba et al. | 356/437 |
| 4,246,773 | 1/1981 | Haruta | 73/24 |

FOREIGN PATENT DOCUMENTS

| | | | |
|---|---|---|---|
| 140249 | 11/1981 | Japan | 73/24 |
| 727891 | 4/1955 | United Kingdom | 73/24 |
| 2027198 | 2/1980 | United Kingdom | 73/24 |

OTHER PUBLICATIONS

G. B. Barton et al., "Developments in Electrochemical Oxygen Meter Probes for Use in Liquid Sodium", *Nuclear Technology*, vol. 57, pp. 315–319, Jun. 1982.

Primary Examiner—Stephen A. Kreitman
Attorney, Agent, or Firm—Ivor J. James, Jr.; Samuel E. Turner; Raymond G. Simkins

[57] ABSTRACT

Sound waves are generated in a sonic cell and propagated through a gas to a sensor which is coupled to a microcomputer. A gas mixture is first directed into a chamber and the attenuation and transit time of sound waves are calculated. Then, a calibrated gas is directed into the chamber, and the attenuation and transit time are again calculated. With these measurements, the microcomputer calculates the concentrations of at least two gaseous constituents such as hydrogen and water vapor, in the gas mixture. The microcomputer acts also as a control for operating valves and heater coils in response to pressure and temperature sensors coupled with the chamber.

8 Claims, 7 Drawing Figures

METHOD AND APPARATUS FOR DETECTING HYDROGEN, OXYGEN AND WATER VAPOR CONCENTRATIONS IN A HOST GAS

BACKGROUND OF THE INVENTION

Gas mixtures of hydrogen, oxygen, water vapor and a host gas, such as nitrogen, commonly exist in nuclear plant containments in varying concentrations, depending upon the design and operational characteristics of the plant. The atmosphere in the containment is usually monitored for $H_2$ and $O_2$ content to assure that explosive mixtures do not arise that might threaten the integrity of the containment. At the present time, means for sensing these gases in the presence of dry nitrogen is provided by electrochemical cells whose active element (the electrolite) is chosen to be sensitive to either $H_2$ or $O_2$, but not both, and to be inert to nitrogen.

Electrochemical cells of the above-mentioned type have limited operating lives and are difficult to qualify for use in the post-accident environment of the containment. Their sensitivity is affected by radiation fields, excessive water vapor, and a variety of contaminants usually found in the containment itself. Complicated and expensive sampling systems are required for their use.

During normal reactor operations, $H_2$ and $O_2$ are produced by electrolysis of water. Tritium is also produced in smaller quantities. Normally, these gases are dissolved in the primary coolant but can accumulate in the containment and the radwaste building over long periods of time. Hydrogen recombiners are provided to handle this source.

Reactor transients can lead to depressurization of the primary system and evolution of the dissolved gases. In the unlikely event that the fuel temperature exceeds about 1500° C., the zirconium fuel cladding can be oxidized by water vapor, releasing large quantities of $H_2$. Certain oxides of zirconium are unstable and can release $O_2$ to the containment atmosphere. Thus, the relative $H_2/O_2$ concentrations can vary widely and possibly reach explosive proportions-above 5 v/o (volume percent) in dry air. The explosive mixture composition is appreciably dependent on water vapor content. Therefore, accurate assessement of hazardous conditions requires knowledge of the local relative humidity as well as the $H_2/O_2$ ratio.

Means for handling large and variable $H_2/O_2$ concentrations rely heavily on the type of sensing method used. Accuracy and reliability are very important, as are insensitivity to radiation and contamination. In view of the drawbacks of prior art techniques, a need has arisen for an improved method of sensing $H_2$, $O_2$, and water vapor in gas samples, especially those taken from a nuclear plant containment for monitoring purposes.

Prior U.S. patents relating to the detection of gases include the following:

| | |
|---|---|
| 3,429,177 | 3,468,157 |
| 3,724,484 | 3,805,590 |
| 3,902,365 | 3,977,394 |
| 3,981,176 | 4,119,950 |
| 4,155,246 | 4,220,040 |
| 4,235,099 | 4,236,827 |
| 4,246,773 | |

U.S. Pat. No. 3,429,177 discloses a method for detecting hydrogen gas using two acoustic waves. Hydrogen can be detected by sensing a change in the velocity between the acoustic waves.

U.S. Pat. No. 3,724,484 discloses a gas detector used in nuclear reactor environments to analyze the density of nuclear particles in hydrogen gas that flows into a reactor cavity. U.S. Pat. No. 3,977,394 is directed to the use of a computer for gas analysis and discloses the use of a spirometer to produce a signal proportional to the volume of air inhaled and exhaled by a person.

U.S. Pat. No. 3,902,365 discloses the use of a tuning fork driven at its natural frequency by a regenerative piezo electric drive; U.S. Pat. No. 4,235,099 discloses a method for measuring the density of a liquid using ultrasonic waves; U.S. Pat. No. 4,236,827 discloses an opto-acoustic gas analyzer using a black body light source and a pressure detector for detecting pressure changes in a gas; and U.S. Pat. No. 3,805,590 discloses a sensor for the partial pressure of oxygen using ultrasonic waves. The remaining patents relate to the art of ultrasonic gas analysis.

SUMMARY OF THE INVENTION

The present invention is directed to a method and apparatus for sensing and determining varying amounts of $H_2$, $O_2$ and $H_2O$ mixed in $N_2$ in a gas sample taken from a gaseous environment, such as a nuclear plant containment. The method uses apparatus currently available to detect and measure $O_2$ concentration, thereby reducing the problem to one of simultaneous measurement of $H_2O$ and $H_2$ in a host gas mixture.

It is known that the speed of sound in a gas held at constant temperature and pressure is a function of its composition, i.e., the masses and volume fractions of the constituents of the gas. In addition, at ultrasonic frequencies, of the order of 50 kHz and above, sound waves are strongly damped by thermal conductivity, diffusion, an viscosity effects, these characteristics also being dependent on the composition of the gas. Thus, for a predetermined $O_2$ concentration a simultaneous and accurate measurement of velocity and damping provides the basis for determining the concentrations of $H_2$ and $H_2O$ in the presence of a host gas, such as $N_2$.

Apparatus has been known in the past for generating and detecting ultrasonic energy for applications in thermometry, ranging and time-domain-reflectometry. Such applications use only velocity measurements but have proven useful in practice. The present invention is based upon this concept and is directed to apparatus and a method in which a sample of gas is drawn into a sonic cell having a heated, insulated and evacuated chamber and held until the gas temperature and pressure equalize to predetermined levels. An ultrasonic transducer is then actuated to cause ultrasonic pulses to be transmitted through the gas sample which is isothermal and isobaric. The pulses are detected at a known, fixed distance from the source of the ultrasonic signal and the transit time and pulse height attenuation of the ultrasonic signal are determined and used with a microcomputer to calculate the concentrations of $H_2$ and water vapor. The resulting data can then be printed out or displayed as desired.

Among the advantages of the present invention is that the apparatus of the invention uses sonic velocity and attenuation simultaneously to derive two variable component concentrations in a gas mixture. The method of the present invention permits the use of a microcomputer to convert non-linear analog signals into linear, digital data appropriate for display and printout. The invention is applicable to any tertiary gas mixture whose constituents are of significantly different masses.

The sonic cell forming a part of the apparatus of the invention is highly reliable and stable in operation. Moreover, it is compact and rugged in construction and can conveniently be operated remotely in hostile environments. It is especially insensitive to radiation and minute amounts of impurities. It is compatible with existing containment systems so as to assure that large system development costs can be avoided.

The primary object of the present invention is to provide an improved apparatus and method for determining varying amounts of gaseous constituents and water vapor in a sample gas taken from a gaseous atmosphere, such as the atmosphere of a nuclear plant containment, so that the concentrations of the gaseous constituents and water vapor in the gas sample can be continuously monitored to assure that undesired mixtures of constituents do not arise that might threaten the integrity of the atmosphere from which the gas sample is taken.

Another object of the present invention is to provide an apparatus and method of the type described wherein ultrasonic pulses are transmitted through the gas sample in a sonic cell after the gas sample has been drawn into the cell from a gaseous atmosphere to be monitored so that the time of transit of ultrasonic pulses through a predetermined distance in the sonic cell and the attenuation of the pulse height of the ultrasonic pulses can be determined and used in calculations by a microcomputer to provide the $H_2$ and water vapor concentrations in the gas sample and to allow the resulting data to be displayed or recorded.

Other objects of this invention will become apparent as the following specification progresses, reference being had to the accompanying drawings for illustrations of the apparatus of the invention and graphic results obtained from operation of the method of the invention.

IN THE DRAWINGS

Figure 1:
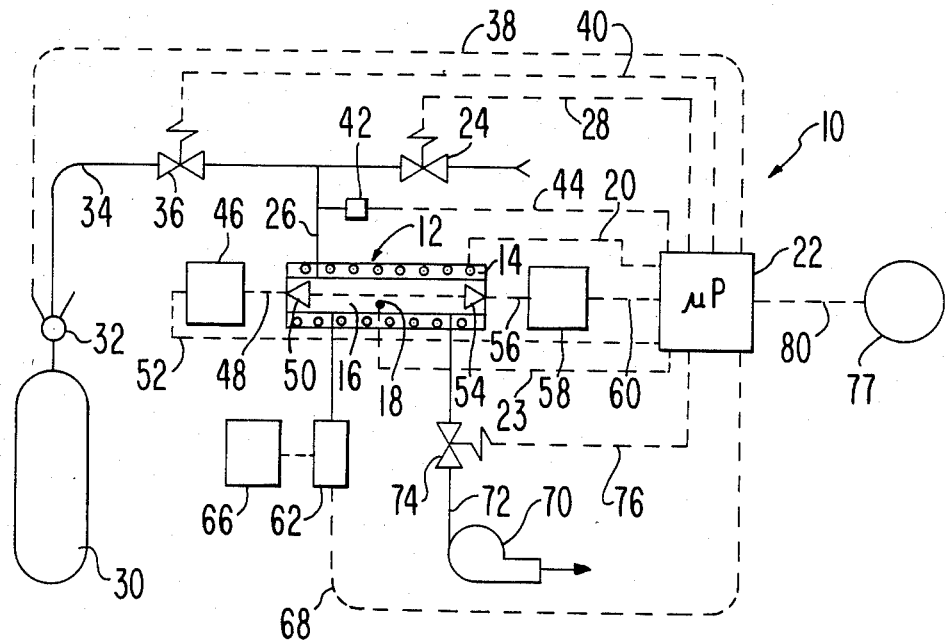
FIG. 1 is a schematic view of a monitoring system using a sonic cell and associated with equipment, including a microcomputer for calculating hydrogen, oxygen and water vapor concentrations in a sample gas.

The monitoring system of the present invention is broadly denoted by the numeral 10 and includes a sonic cell 12 defined by an outer wall 14 which defines a heated, insulated jacket presenting a closed chamber 16 for receiving a gas sample to be analyzed. Wall 14 has an internal heater therein to heat the gas in chamber 16. The heater is in the form of heating coils, and the temperature in chamber 16 is sensed by a thermocouple 18. The heater is coupled by an electrical lead 20 to a microcomputer 22, and the microcomputer controls the heater in wall 14. The heating coil is operated by the microcomputer in response to the temperature sensed by thermocouple 18, the latter being coupled by an electrical lead 23 to microcomputer 22.

A gas sample from a gaseous atmosphere, such as a nuclear plant containment, is coupled by solenoid valve 24 through an inlet pipe 26 to chamber 16. Solenoid 24 is coupled by an electrical lead 28 to the microcomputer and is controlled thereby. A calibration gas sample is supplied from a tank 30 coupled by a pressure regulator 32, pipe 34 and solenoid valve 36 to inlet pipe 26 connected to chamber 16. Pressure regulator 32 and valve 36 are coupled by electrical leads 38 and 40, respectively, to the microcomputer and are controlled thereby. A pressure sensor 42 coupled with inlet pipe 26 senses the internal fluid pressure of chamber 16. Pressure sensor 42 is coupled by an electrical lead 44 to the microcomputer 22 and is controlled thereby.

Figure 2:
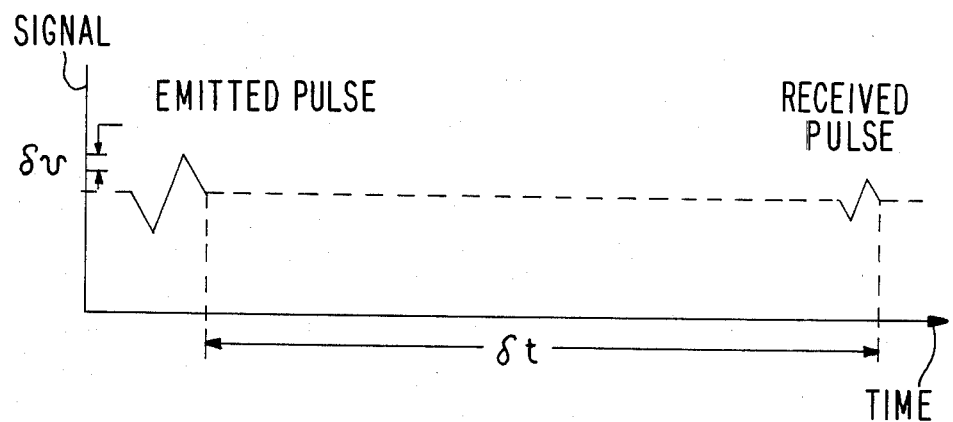
FIG. 2 is a graphic representation of a number of ultrasonic pulses versus time, showing the attenuation of the pulses during a predetermined transit time through a sample gas.

Pulsing electronics 46 has a signal output coupled by an electrical lead 48 to an ultrasonic transducer 50 at one end of chamber 16, transducer 50 being operable to generate a series of ultrasonic pulses in the gas in chamber 16. FIG. 2 depicts series of such pulses in which the pulse height is plotted versus time of transit through chamber 16. Pulsing electronics 46 is coupled by an electrical lead 52 to microprocessor 22 and is controlled thereby.

A sonic detector 54 is coupled to the opposite end of chamber 16 in alignment with transducer 50 so as to receive ultrasonic pulses therefrom after the signals have been attenuated by the gas sample in the chamber 16. FIG. 2 also shows attenuation of the pulse height of the pulses reaching detector 54. Detector 54 is coupled by an electrical lead 56 to signal conditioning electronics 58, the latter in turn being coupled by an electrical lead 60 to microcomputer 22.

An oxygen sensor 62 has a tube 64 communicating with chamber 16. Oxygen sensor 62 has an electronics device 66 for actuating sensor 62 when a signal from microprocessor 22 is directed along an electrical lead 68 to sensor 62. Oxygen sensor 62 can be of any conventional type. There are suitable sensors commercially available, which are sensitive to only oxygen. One such sensor operates on the principle of detecting the magnetic moment of the $O_2$ molecule and relating the measured diamagnetism to the oxygen concentration in the sample. This approach results in oxygen measurements which are independent of the presence of other gaseous species. Such a sensor is suitable for the purpose of determining the concentration of $O_2$ in a sample gas in chamber 16.

A continuously running metal bellows pump 70 is coupled through pipe 72 and a solenoid valve 74 to chamber 16 for exhausting the chamber of gas when valve 74 is opened. An electrical lead 76 couples valve 74 to microcomputer 22 and is controlled thereby. A display device 77 is coupled with microcomputer 22 by an electrical lead for displaying the calculations representing the concentrations of $H_2$, $O_2$ and water vapor in a host gas in chamber 16, such as nitrogen.

In the operation of system 10, gas sensing can be controlled from a local panel adjacent to the location of the sonic cell 12, such as inside a nuclear plant containment. System 10 is especially configured to operate automatically in situ under normal circumstances and in post-accident conditions described in USNRC Regulatory Guide 1.97.

As shown in FIG. 1, the sonic cell is heated after a sample gas is directed from a source through solenoid valve 24 and into chamber 16. The pulsing electronics 46 is actuated along with detection and signal conditioning electronics 58 at the appropriate times, determined by the software of the microcomputer. This provides the input data to the microcomputer in the form of ultrasonic pulses sensed by detector 54 after the pulses have passed through and have been attenuated by the gas sample. Typically, the sonic cell can be 30 inches long and 1 inch diameter. The ultrasonic frequency generated by transducer 50 is typically 200 kHz.

The microcomputer 22 determines when the pressure and temperature are at predetermined operating values in chamber 16. The pressure is determined by pressure transducer 42, and the temperature is sensed by thermocouple 18.

Pipe 72 provides means for evacuating chamber 16 when solenoid valve 74 is opened under the control of the microcomputer. This occurs when solenoid valves 24 and 36 are closed. By closing valves 36 and 74 and opening valve 24, a gas sample is drawn into chamber 16 from a gaseous atmosphere for analysis. In the alternative, solenoid valve 36 is opened when valves 24 and 74 are closed to allow a calibration gas into chamber 16 from tank 30 whose pressure regulator 32 is controlled by the microcomputer. The sequencing of all solenoid valves is achieved by the operation of the microcomputer. Oxygen sensor 62 provides an independent measurement of $O_2$ concentration to the microcomputer. The input data to the microcomputer is processed in accordance with the flowcharts of FIGS. 3A and 3B, and the gas concentrations calculated by the operation of the microcomputer are displayed remotely by the display device 77.

It is to be noted that the microcomputer 22 serves two functions in system 10: It operates as controller of temperature, flow and pressure; and it operates as a data collector and analyzer.

Figure 3A:
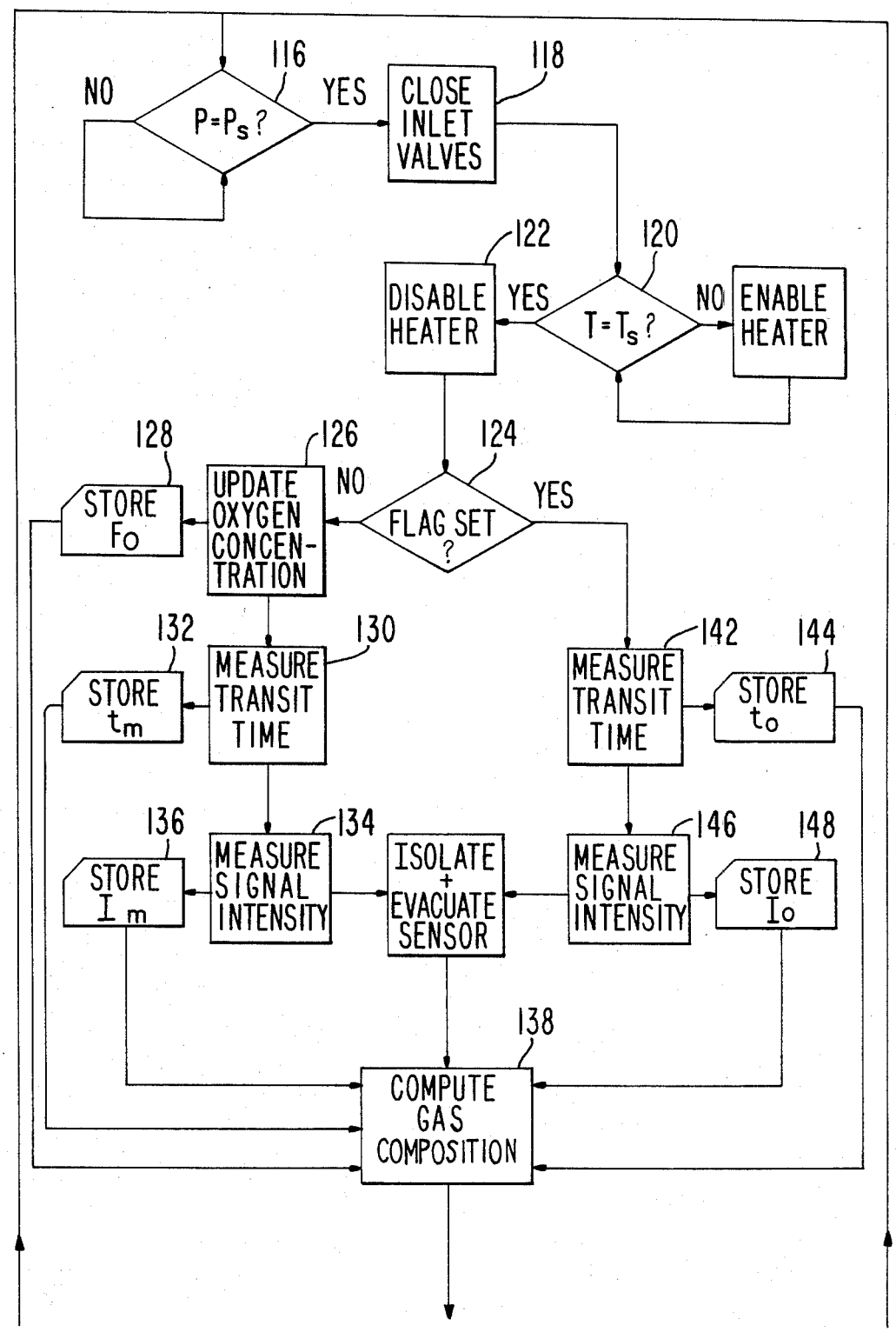
FIG. 3A is a flowchart showing a part of the algorithm of the present invention for the calculation of gas constituent concentrations using a microcomputer.
Figure 3B:
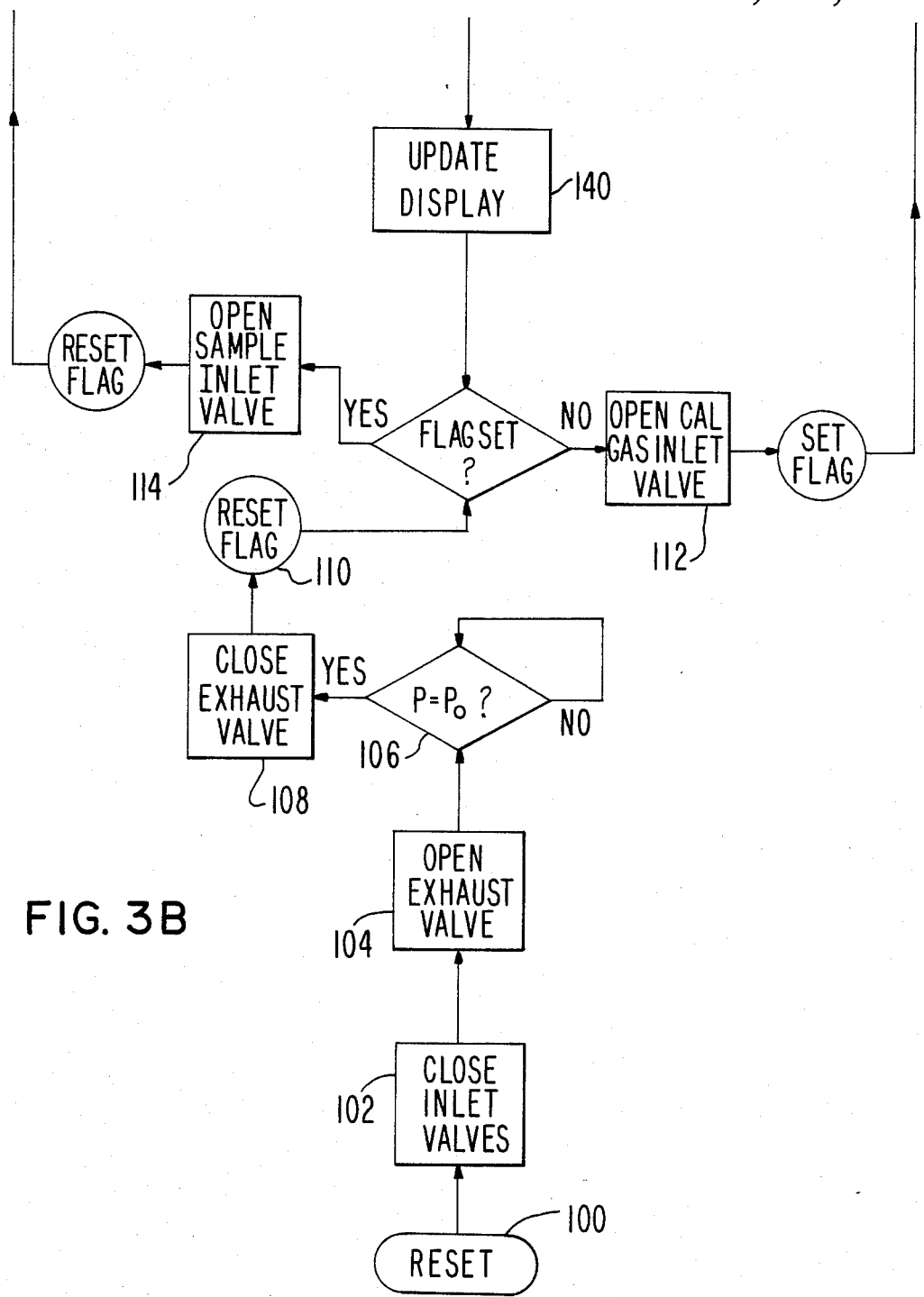
FIG. 3B is a flowchart showing the remainder of the algorithm shown partially in FIG. 3A.

The microcomputer logic is shown in the flowchart of FIGS. 3A and 3B for cyclical auto-calibration and sample analysis. The computing relationships used in system 10 are as follows:

$F_H = a_1 + a_2 F_O + a_3 (I_m/I_o) - a_4 (t_m/t_o)^2$ $F_W = -b_1 - b_2 F_O - b_3 (I_m/I_o) + b_4 (t_m/t_o)^2$ where: $F_O$ = measured $O_2$ concentration (v/o)
$F_H$ = calculated $H_2$ concentration (v/o)
$F_W$ = calculated $H_2O$ concentration (v/o)
$I_m$ = measured sonic intensity for gas mixture (mv)
$I_o$ = measured sonic intensity for cal gas (mv)
$t_m$ = measured sonic transit for gas mixture (ms)
$t_o$ = measured sonic transit time for cal gas (ms)

The coefficients $a_i$ and $b_i$ are determined by the temperature, pressure, geometry, and sonic frequency used in system 10. Typical values are given in Table 1 for room temperature gas and a pressure of one atmosphere in a sonic cell 30 inches long by one inch in diameter and sonic signal at 200 kHz.

TABLE 1

| i | $a_i$ | $b_i$ |
| --- | --- | --- |
| 1 | 1.279 | 0.5243 |
| 2 | 0.200 | 0.1190 |
| 3 | 0.034 | 0.0890 |
| 4 | 1.313 | 0.6133 |

The foregoing relationships show that, in the range of interest, the ratios of pulse transit times and pulse intensities are the relevant parameters to be measured. These measurements are typically in the following ranges:

$0.3 \leq (I_m/I_o) \leq 1$
$0.95 \leq (t_m/t_o) \leq 1.02$
$0 \leq F_O \leq 0.21$ Operation should be limited to these ranges since outside these ranges the relationships may not be valid. Therefore, the microcomputer software is typically programmed to make a validity check and provide an alarm when one or more of these limits is violated.

The ranges of volume fractions measurable with system 10 are as follows:

$0 \leq F_H \leq 0.10$ $0 \leq F_W \leq 0.03$ (100% RH @ 68° F.)

using these relationships. The upper limit on water vapor is dictated by saturation conditions at room temperature at atmospheric pressure. Naturally, this limit will be a function of several operating conditions and is given here for reference only. Useful oxygen sensors are not limited in range and give results independent of the presence of hydrogen and water vapor. This results from the oxygen sensor design, which is not sonic in nature.

The sonic cell 12 of this invention can have means for discriminating against reflected sonic energy within chamber 16. For example, the interior surfaces of cell 12 can be provided with an anechoic coating to minimize or substantially eliminate reflected sonic energy. In practice, this has not been necessary when careful alignment is exercised.

Sonic velocity measurements using system 10 confirm the excellent accuracy obtainable with $H_2/N_2$ mixtures. Table 2 shows the measured pulse transit time ratio for pure $N_2$ and the indicated gas sample or mixture versus the computed square-root of the mass ratio.

TABLE 2

SONIC VELOCITY MEASUREMENTS IN $H_2/N_2$ MIXTURES OF 68° F. (200 kHz)

| $H_2$ concentration (v/o) | $\delta t_{N_2} / \delta t_{mix}$ | $M_{N_2} / M_{mix}$ | % difference |
| --- | --- | --- | --- |
| 1.0 | 1.0046 | 1.0047 | 0.01 |
| 1.58 | 1.0072 | 1.0074 | 0.02 |
| 2.50 | 1.0117 | 1.0118 | 0.01 |
| 3.20 | 1.0153 | 1.0152 | 0.01 |
| 4.30 | 1.0206 | 1.0206 | 0.00 |
| 5.30 | 1.0251 | 1.0259 | 0.078 |
| 6.20 | 1.0315 | 1.0301 | 0.16 |
| 7.10 | 1.0362 | 1.0347 | 0.14 |
| 8.10 | 1.0430 | 1.0398 | 0.31 |
| 9.10 | 1.0491 | 1.0451 | 0.38 |
| 9.90 | 1.0550 | 1.0494 | 0.53 |

Agreement is obtained to less than $\frac{1}{2}$% difference using certified gas mixtures. It is significant that the agreement is best at the lower $H_2$ concentration. The conclusion is that accuracy, repeatability and sensitivity are excellent for binary mixtures.

Figure 4:
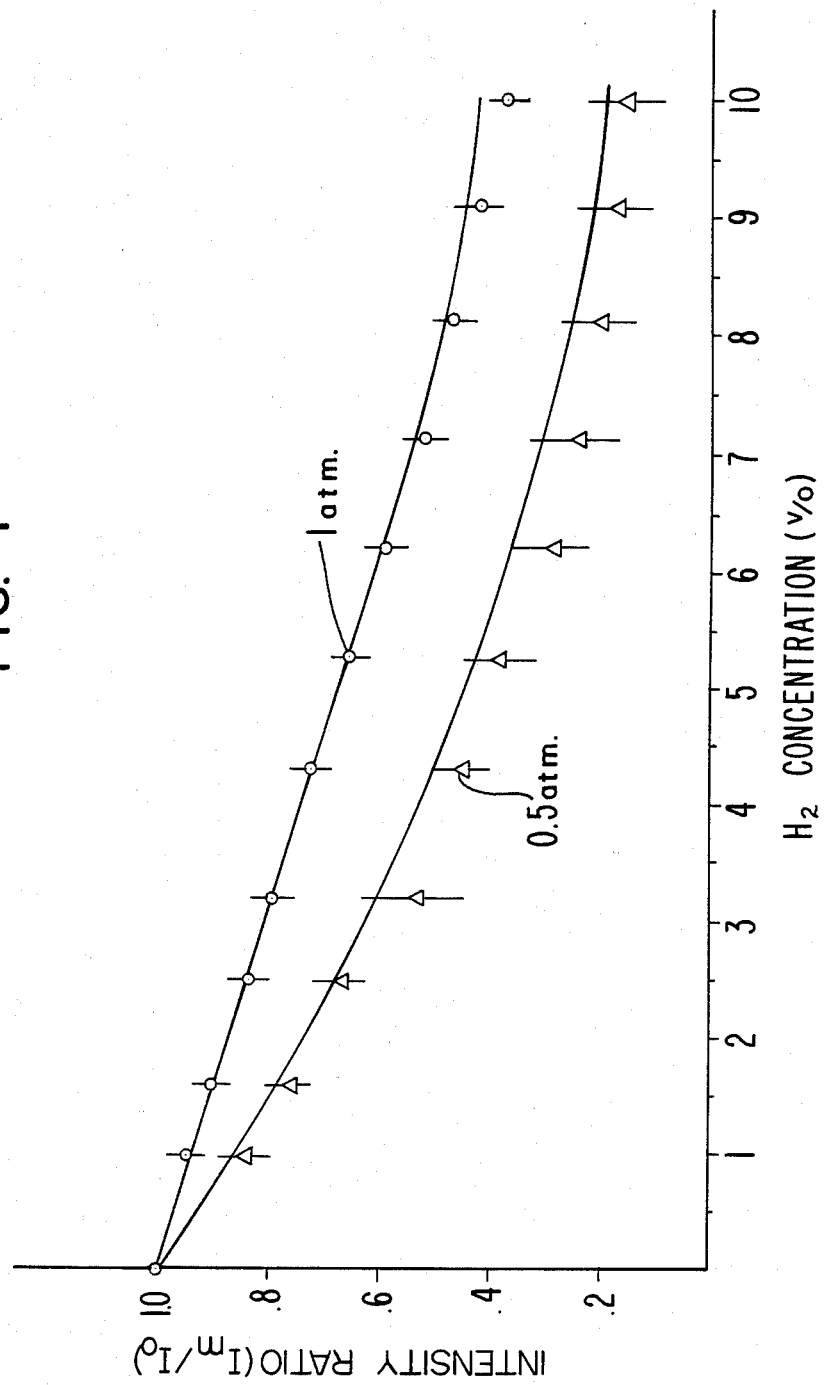
FIGS. 4–6 are graphic views showing the results achieved with the use of the method of the present invention.

Results of attenuation measurements are shown in FIG. 4 for two values of cell pressure. Good sensitivity and repeatability were obtained, especially at a pressure of 1 atm. At lower pressures, the data is more affected by noise so that agreement with theory is not as good. The preferred operating pressure is 1 atm.

An important absorption mechanism for mixtures containing $H_2$ is the so-called diffusion term. This term means that as the wave motion occurs in the gas sample in cell 12, the light hydrogen molecules react to density gradients occurring in time and diffuse out of the wave, thereby damping its amplitude. This turns out to be the dominant loss mechanism in the sonic cell 12.

Figure 5:
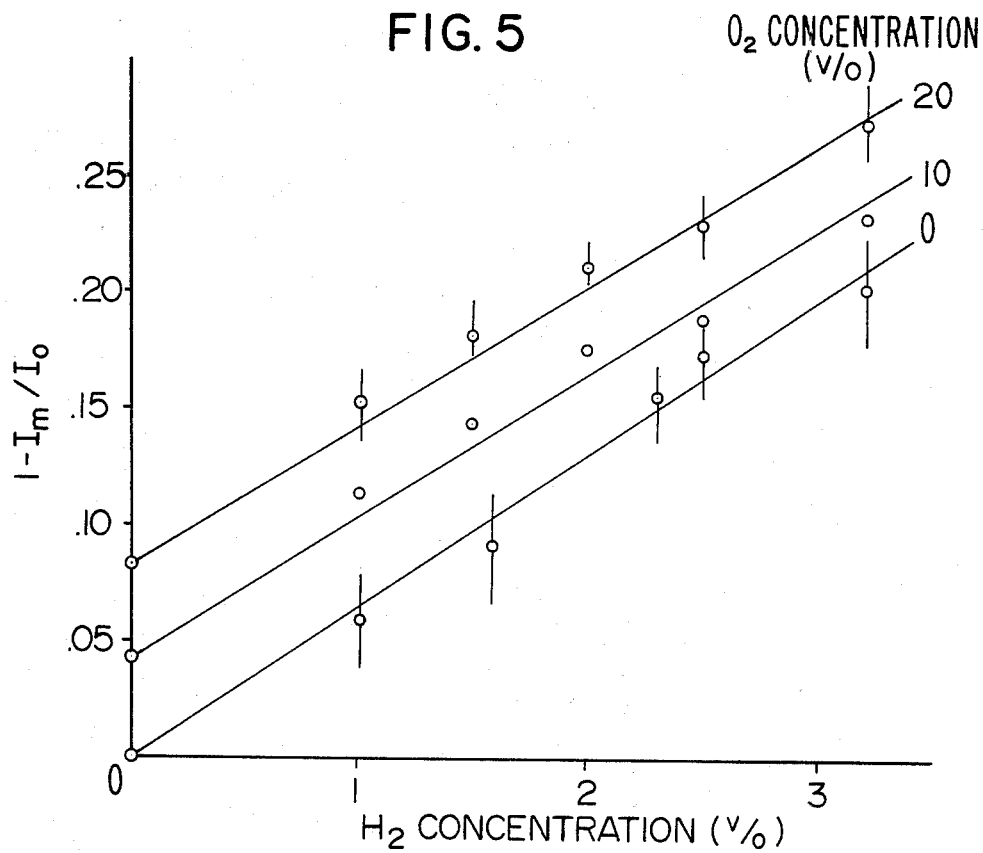
Figure 6:
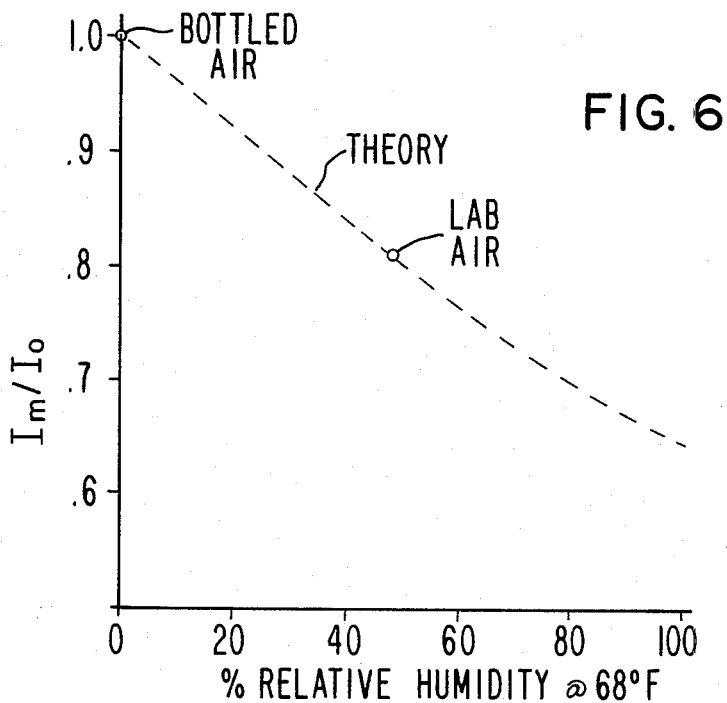

The effect of oxygen molecules was studied by using certified mixtures of $H_2$, $O_2$ and $N_2$. The calibration was made using pure nitrogen as in FIG. 4. herein. For safety reasons, the maximum hydrogen concentration obtainable was 3.2 v/o with oxygen present. The results of these attenuations measurements are shown in FIG. 5, along with the theoretical fit. Again good repeatability and sensitivity were obtained. The system 10 is considerably less sensitive Finally, a very qualitative result relating to the sensitivity to water vapor was obtained by comparing the attenuation in dry air (bottled) to that in laboratory air with measured relative humidity. Only one point could be measured (since the lab was air conditioned), but this was extrapolated using the theoretical model for air/water vapor mixtures. The result is shown in FIG. 6 wherein the intensity is normalized to dry air. It is to be noted that system 10 is quite sensitive to water vapor which implies the need for accurate measurement of the local relative humidity.

In summary, system 10 provides a simple, highly reliable and rugged approached to the sensing of nuclear containment and other atmospheres. The system is extremely sensitive to water vapor and hydrogen, but less sensitive to oxygen. Thus, if oxygen is to be measured independently, such as with sensor 62 (FIG. 1), the sonic cell 12 could be used to simultaneously measure hydrogen and water vapor content. These three pieces of data are very useful in predicting flammability conditions in post-accident nuclear containment environments, as well as other applications.

Microcomputer 22 can of any suitable type. For instance, it can be an Intel 8086 with a floating point arithmetic module.

In the flowchart of FIGS. 3A and FIGS. 3B, the method of the present invention comprises a number of steps beginning with the reset step 100, following which inlet valves 14 and 36 are closed at step 102. Exhaust valve 74 is opened at step 104 and the microcomputer determines, at step 106, whether the fluid pressure P in sonic cell 12 is at a predetermined exhaust value $P_o$. If so, exhaust valve 74 is closed at step 108, a first flag is reset at step 110. If the flag is not set, valve 36 is opened at step 112 to control the flow of calibrated gas into sonic cell 12 from tank 30. If the flag is set, which it initially is, valve 24 is opened at step 114 so that a sample, or pure host gas, can be directed into sonic cell 12.

Depending upon whether valve 24 or 36 is opened, the next step is a decision by the microcomputer as to whether the sonic cell pressure P is pressurized with the particular gas to a predetermined pressure $P_s$. This occurs at step 116 (FIG. 3a). If the pressure has reached this predetermined value, the inlet valve is closed at step 118 and the computer at step 120 determines the temperature T of the gas in sonic cell 12. If the temperature is at the proper value $T_s$, the heater in sonic cell 12 is turned off at step 122 and the microcomputer determines whether a second flag has been set at step 124. Typically, the flag is not set initially so that the oxygen sensor 62 is actuated to determine the oxygen content in sonic cell 12. This is done at step 126, and the determined oxygen concentration $F_O$ is stored in memory at step 128. Next, and ultrasonic pulse is transmitted through the gas in the sample cell, and the transit time of the pulse through the gas sample is measured at step 130. This time $t_m$ is stored in memory at step 132. The microcomputer also measures the attenuation or the signal intensity of the pulses at step 134 and stores the measured intensity $I_m$ at step 136 in memory. Using the information stored in steps 128, 132 and 136, the microcomputer calculates the hydrogen and water vapor concentrations in the sample gas at step 138. Then, the diaplay 77 (FIG. 1) is provided with the information and displays the calculated results at step 140.

The next step is to determine that the first flag is not set after step 110, in which case the calibration gas is directed into the sonic cell upon opening of valve 36 at step 112. The steps 116, 118, 120 and 122 are repeated and at step 124, the second flag is set so that the ultrasonic pulses are directed through the calibrated gas. The microcomputer computes the transit time through the calibration gas at step 142, and the transit time $t_o$ for the calibration gas is stored at step 144 in memory. The microcomputer also measures the attenuation or intensity of the ultrasonic pulses at step 146 and stores the measured sonic intensity for the calibration gas at step 148. With the stored information of steps 128, 132, 136, 144 and 148, the relationships for the determination of hydrogen and water vapor concentrations are solved and the resulting information is displayed at step 140.

What is claimed is:

1. Apparatus for analyzing samples of an atmoshere drawn from the containment of a nuclear plant, said atmosphere being substantially constituted of varying concentrations of first, second and third constituent gases diffused in a host gas, said apparatus being operative to determine the concentrations of said first, second and third constituent gases in said host gas, said apparatus comprising:

a sonic cell for holding a fixed volume of gas;
   first means coupled with said sonic cell for introducing unknown samples of said containment atmosphere into said sonic cell;
   second means coupled with said sonic cell for introducing calibration samples from an atmosphere of known concentrations of said constituent gases difussed in said host gas into said sonic cell;
   means for establishing said samples at a standard, predetermined temperature and pressure;
   means for directly ascertaining the concentration of said third constituent gas in said samples;
   ultrasound generating means disposed in said sonic cell;
   ultrasound receiving means disposed in said sonic cell a predetermined distance from said generating means;
   exhaust means for discharging samples from said sonic cell;
   means coupled with said receiving means and said third constituent gas gas ascertaining means for calculating the concentrations of said second and third constituent gases in said samples in response to the attenuation factor and the transit time of ultrasonic waves propagated through said unknown samples across said predetermined distance, the concentration of said third constituent gas and the attenuation factor and the transit time of ultrasonic waves propagated through a calibration sample;

said calculating means being coupled with said first means, second means, third gas ascertaining means, ultrasound generating means and exhaust means for controlling or monitoring the operation thereof; and means coupled to the calculating means for displaying the calculated results.

2. Apparatus as set forth in claim 1, wherein said third constituent gas ascertaining means comprises means for determining the oxygen concentration in a gas mixture, said calculating means being operable in response to the magnitude of the oxygen concentration determined by said oxygen determining means.

3. Apparatus as set forth in claim 2, wherein said calculating means comprises a microcomputer coupled to said oxygen determining means for monitoring the oxygen concentration determined thereby.

4. Apparatus as set forth in claim 3, wherein said calculating means further comprises pressure monitoring means and temperature monitoring means coupled to said microcomputer for monitoring said pressure and said temperature.

5. Apparatus as set forth in claim 4, wherein said sonic cell has an inlet and a pipe coupled with said inlet, said pipe adapted to be coupled with a source of said gas mixture, and operable valve means coupled with said pipe for controlling the volume rate of flow of said gas mixture through the pipe, said calculating means being coupled with said valve means for controlling the operation thereof in response to monitored pressure.

6. Apparatus as set forth in claim 5, wherein said calculating means comprises a microcomputer having means for generating a control signal, and means coupling the control signal to said valve means for operating the same.

7. A method employing a sonic cell, including ultrasonic generating means at a first location in said sonic cell and ultrasonic receiving means at a second location in said sonic cell, for the determination of the concentrations of first and second constituent gases in an atmosphere with the aid of digital data processing means, said method comprising the steps of:

providing said digital data processing means with a data base for said sonic cell including at least, measured sonic intensity ($I_o$) for a calibration gas of ultrasonic waves generated at said first location and received of said second location, measured sonic transit time ($t_o$) for said calibration gas from said first location to said second location, predetermined pressure and temperature operating points, vectors of coefficients $a_i$ and $b_i$ related to said predetermined pressure and temperature operating points, the geometry of said sonic cell and the employed sonic frequency, for said first and second constituent gases, respectively, and third constituent gas concentration data ($F_o$) for said sample when said third constituent gas is subject to variation in concentration;

exhausting said sonic cell;

coupling said sonic cell to said atmosphere in order to admit a sample;

monitoring the pressure in said sonic cell and providing the pressure indication to said digital data processing means, said means being programmed to isolate said sonic cell from said atmosphere when the pressure in said cell is substantially equal to said predetermined operating point;

monitoring the temperature of said sample and providing said temperature indication to said digital data processing means, said digital data processing means being programmed to turn on heating means in response to said temperature indication until the temperature of said sample equals said predetermined temperature operating point;

generating ultrasonic waves at said first location in said sonic cell;

receiving said generated ultrasonic waves at said second location in said sonic cell;

determining the sonic transit time ($t_m$) from said first location to said second location for said waves in said sample and providing the same to said digital data processing means;

measuring the intensity of ($I_m$) said sonic waves at said second location and providing the same to said digital data processing means;

calculating in said digital data processing means the equations $$F_h = a_1 + a_2 F_o + a_3 (I_m/I_o) + a_4 (t_m/t_o)^2$$

$$F_w = b_1 + b_2 F_o + b_3 (I_m/I_o) + b_4 (t_m/t_o)^2$$

where $F_h$ is the concentration ratio for said first constituent gas, and $F_w$ is the concentration ratio for said second constituent gas;

displaying the results of the above calculation on a display provided for that purpose;

repeating the aforesaid steps periodically.

8. A method for determining the concentrations of first and second constituent gases in an atmosphere, employing a sonic cell including a first ultrasonic transducer for generating ultrasonic waves in a medium introduced to said sonic cell and a second ultrasonic transducer for receiving ultrasonic waves propagated in said medium and a digital data processor, said method comprising the steps of:

providing said digital data processor with a data base for said sonic cell including at least, predetermined pressure and temperature operating points, and vectors of coefficients $a_i$ and $b_i$ determined by said temperature operating point, said pressure operating point, the geometry of said sonic cell and the frequency generated by said first ultrasonic transducer;

exhausting said sonic cell;

coupling said sonic cell to a source of a calibration gas until the pressure of said calibration gas in said sonic cell substantially reaches said predetermined pressure operating point;

heating said sonic cell until said calibration gas reaches said predetermined temperature operating point;

generating ultrasonic waves of standard intensity with said first ultrasonic transducer;

detecting said generated ultrasonic waves with said second ultrasonic transducer;

measuring the intensity ($I_o$) of said sonic waves at said second ultrasonic transducer and providing said measurement to said digital data processor;

determining the sonic transit time ($t_o$) for sound waves from said first ultrasonic transducer to said second ultrasonic transducer and providing said determination to said digital data processor;

exhausting said sonic cell;
coupling said sonic cell to said atmosphere to be analyzed until the pressure in said sonic cell is substantially equal to said predetermined pressure operating point thus providing a sample of said atmosphere for analysis;
heating said sonic cell until said sample gas reaches said predetermined temperature operating point;
providing an oxygen concentration sensor adapted to generate oxygen concentration data ($F_o$) for said sample;
generating ultrasonic waves at a first location in said sonic cell;
detecting said generated ultrasonic waves at a second location in said sonic cell;
measuring the intensity ($I_m$) of said sonic waves at said second location and providing said measurement to said digital data processor;
determining the sonic transit time ($t_m$) for soundwaves, from said first location to said second location and providing said determination to said digital data processor;
exhausting said sonic cell;
calculating in said digital data processor the equations $$F_h = a_1 + a_2 F_o + a_3(I_m/I_o) + a_4(t_m/t_o)^2$$

$$F_w = b_1 + b_2 F_o + b_3(I_m/I_o) + b_4(t_m/t_o)^2$$

where $F_h$ is the concentration ratio for said first constituent gas, and
$F_w$ is the concentration ratio for said second constituent gas;
displaying the results of the above calculation on a display provided for that purpose; and
periodically repeating the aforesaid steps.

* * * * *